US00PP22094P2

(12) United States Plant Patent
Gossett

(10) Patent No.: US PP22,094 P2
(45) Date of Patent: Aug. 23, 2011

(54) *SEDUM* PLANT NAMED 'CRYSTAL PINK'

(50) Latin Name: *Sedum spectabile*
Varietal Denomination: Crystal Pink

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/800,258

(22) Filed: May 11, 2010

(51) Int. Cl.
*A01H 5/00* (2006.01)

(52) U.S. Cl. ..... Plt./479

(58) Field of Classification Search ..... Plt./479
See application file for complete search history.

*Primary Examiner* — June Hwu

(74) *Attorney, Agent, or Firm* — Klarquist Sparkman LLP

(57) ABSTRACT

A new and distinct *Sedum spectabile* plant characterized by large, light pink flower heads, a short stature with strong upright stems, and excellent vigor.

1 Drawing Sheet

Botanical classification: *Sedum spectabile.*

Variety denomination: 'Crystal Pink'.

The present invention relates to a new and distinct cultivar of *Sedum spectabile* and given the cultivar name of 'Crystal Pink'. *Sedum* is in the family Crassulaceae. *Sedum* 'Crystal Pink' originated as a seedling from an open pollinated proprietary *Sedum spectabile.*

Compared to *Sedum spectabile* 'Brilliant', an unpatented plant, *Sedum* 'Crystal Pink' is shorter with light pink flowers rather than rose pink.

Compared to *Sedum spectabile* 'Hot Stuff' (U.S. Plant Pat. No. 17,212), *Sedum* 'Crystal Pink' has a larger plant size and light pink rather than purple red flowers.

Stems of the new variety do not fall over after bloom.

This new and unique *Sedum* is distinguished by:

1. large, light pink flower heads,
2. short stature with strong upright stems,
3. and excellent vigor.

This new cultivar has been reproduced only by asexual propagation (cuttings, division, and tissue culture). Each of the progeny exhibits identical characteristics to the original plant. Asexual propagation by cuttings, division, and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a two-year-old *Sedum* 'Crystal Pink' growing in the field in September in Canby, Oreg.

DETAILED PLANT DESCRIPTION

The following is a detailed description of the new *Sedum* based on observations of a two-year-old specimen grown in the ground in full sun under typical outdoor conditions in the trial fields in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, 5$^{th}$ edition.

Plant:

*Type.*—Herbaceous perennial.
*Hardiness.*—USDA Zone 4 to 9.
*Size.*—35 cm tall from the ground to the top of the foliage and 38 cm wide.
*Habit.*—Clump forming.
*Root description.*—Multiple fleshy roots from each crown, White 155A, grows to 5 mm wide and 20 cm long in clay loam soil.
*Vigor.*—Excellent.

Stem:

*Height.*—20 cm, unbranched.
*Width.*—2.4 cm.
*Color.*—Green 138B.
*Texture.*—Succulent.
*Surface.*—Glaucous.

Leaf:

*Type.*—Simple, cauline, succulent.
*Arrangement.*—Opposite.
*Shape.*—Broadly obovate.
*Venation.*—Pinnate.
*Margins.*—Entire.
*Apex.*—Obtuse.
*Base.*—Cuneate.
*Blade size.*—Grows to 7.5 cm long and 5 cm wide.
*Surface.*—Glaucous on bottom side, glabrous on top side.
*Shininess.*—Matte.
*Texture.*—Thick, spongy, succulent.
*Petiole.*—On lowest leaves only, 1 cm long and 3 mm wide, Green 138B.
*Leaf color.*—Topside Green 138A; bottom side Greyed Green 191B.

Inflorescence:

*Type.*—Terminal, flat topped, branched, dense, corymbose cyme.
*Number of flowers.*—100 to 250 per stem.
*Size.*—10 cm to 17 cm wide and 10 cm to 15 cm deep.

*Peduncle.*—21 cm tall and 14 mm wide, glaucous, Green 138B.

*Pedicel.*—Variable, glaucous, Green 138B.

*Bloom period.*—September through October in Canby, Oreg.

Flower bud:

*Size.*—3 mm wide, 6 mm deep.

*Description.*—Ovoid.

*Color.*—White N155B on bottom half and Purple 76D on top half.

Flower:

*Type.*—Complete, actinomorphic.

*Shape.*—Stellate.

*Size.*—1 cm deep and 1.5 cm wide.

*Corolla description.*—5 petals, each grows to 9 mm long, 1.8 mm wide, shape lanceolate with acute tips, entire margins, glabrous on both sides, topside Purple 75C, bottom side White N155B.

*Calyx description.*—5 lobes, divided 4/5 to the base, campanulate, 3.3 mm deep and wide, both sides Greyed Green 191B.

*Stamen description.*—8 in number, 9 mm long, filaments 8 mm long, White N155B, anthers Red Purple 72B, pollen Greyed Purple 187A.

*Pistil description.*—4 mm wide and 6 mm deep, separate prominent carpels, each 6 mm deep and 1 mm wide, Purple 75B.

*Fragrance.*—None.

*Lastingness.*—Each inflorescence lasts 1 month.

Fruit:

*Type.*—Ventrally dehiscent follicle, erect, attenuate.

*Fertility.*—Low.

*Color.*—Brown 200A.

Seed:

*Shape.*—Narrowly oval, somewhat winged.

*Size.*—0.6 mm long.

*Color.*—Brown 200A.

Disease and pest resistance: *Sedum* are susceptible to root rots, scale and mealy bugs. No special resistance has been noted.

I claim:

1. A new and distinct hybrid of *Sedum* plant as herein illustrated and described.

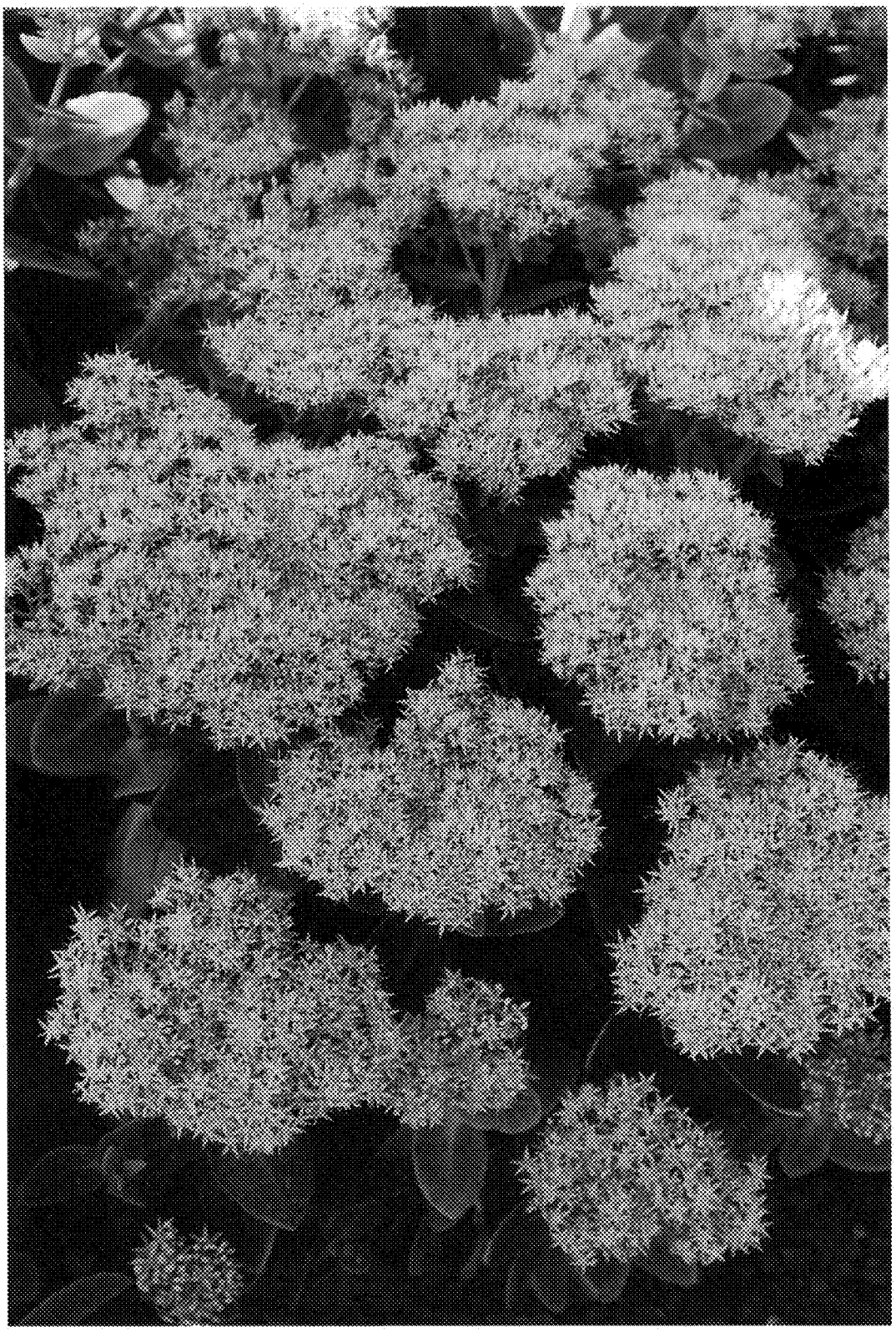

* * * * *